United States Patent [19]

Hayes

[11] Patent Number: 5,001,260

[45] Date of Patent: Mar. 19, 1991

[54] TETRACARBOXYLIC ACIDS

[75] Inventor: Kathryn S. Hayes, Norristown, Pa.

[73] Assignee: Union Camp Corporation, Wayne, N.J.

[21] Appl. No.: 818,221

[22] Filed: Jan. 13, 1986

[51] Int. Cl.$^5$ .................. C07C 51/353; C07C 57/02
[52] U.S. Cl. .................. 562/595; 562/509; 562/590
[58] Field of Search .............. 562/595, 590, 509; 260/407

[56] References Cited

U.S. PATENT DOCUMENTS

| | | |
|---|---|---|
| 2,793,219 | 5/1957 | Barrett et al. ............ 260/407 |
| 2,793,220 | 5/1957 | Barrett et al. ............ 260/407 |
| 3,873,585 | 3/1975 | Sturwold et al. ......... 260/407 |

*Primary Examiner*—Vivian Garner
*Attorney, Agent, or Firm*—Edward J. Sites

[57] ABSTRACT

A process for polymerizing unsaturated dicarboxylic acids comprises heating the acids in the presence of a catalytic proportion of an unactivated clay and water. The product dimer is distilled to separate unreacted monomer acids. The product dimers of 36, 40 and 44 content are useful as corrosion inhibitors, epoxy resin curing agents, lubricants and intermediates for synthetic polymeric resins and polymeric resin plasticizers.

12 Claims, 1 Drawing Sheet

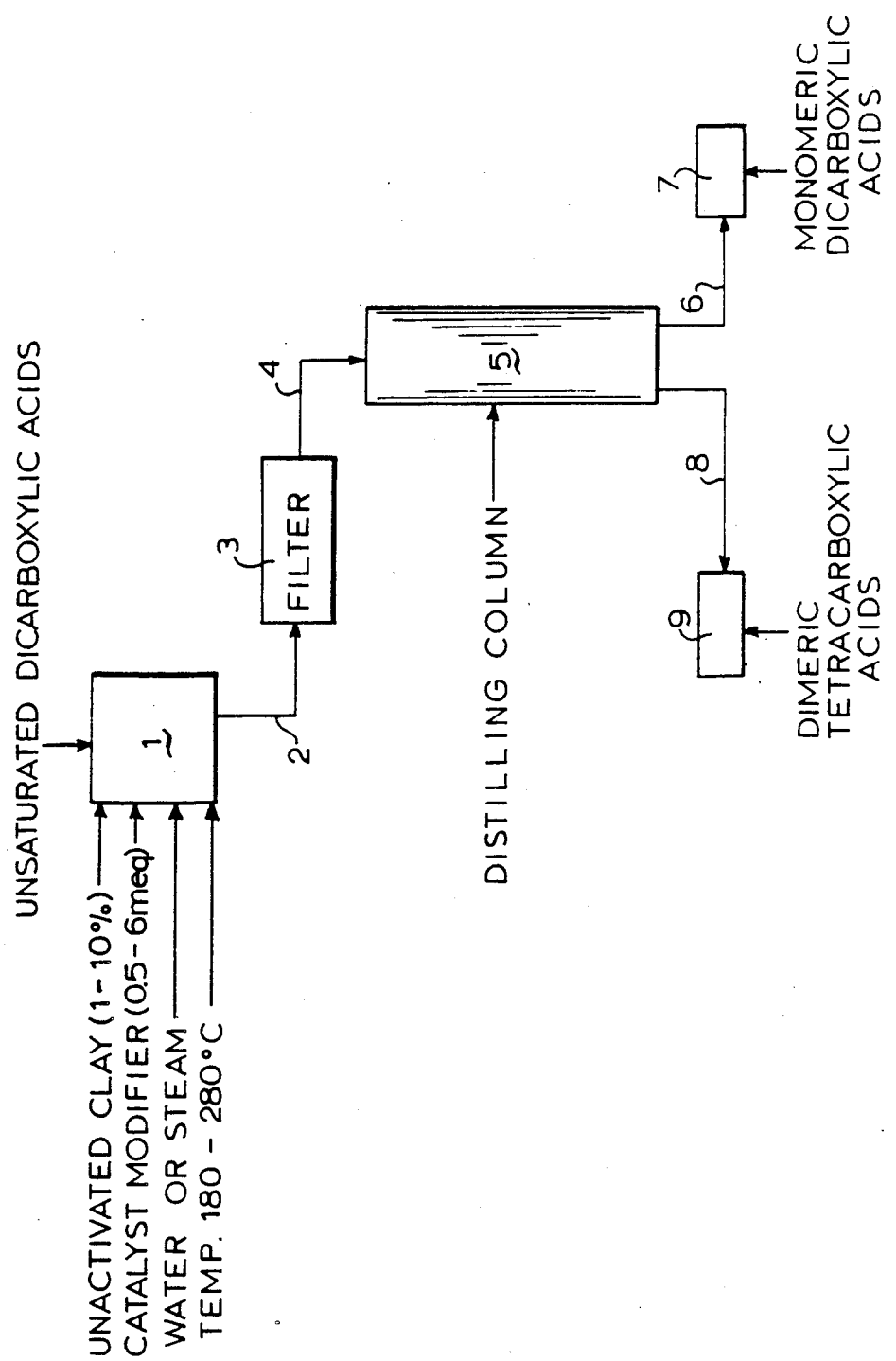

TETRACARBOXYLIC ACIDS

BACKGROUND OF THE INVENTION

1. Field of the Invention

The invention relates to polymerized dicarboxylic acids and more particularly relates to the dimers of unsaturated dicarboxylic acids containing 16, 17, 18, 20, and 22 carbon atoms.

2. Brief Description of the Prior Art

It is well known that monomeric unsaturated fatty acids which are derived from natural sources are capable of being polymerized to the dimerized and trimerized form. This is usually realized by heating such unsaturated fatty acids in the presence of catalytic proportions of a mineral clay and, preferably, an acid-treated mineral clay, at temperatures in excess of about 180° C. in an aqueous environment under autogenous pressure. Representative of the prior art teachings are those found in the U.S. Pat. Nos. 2,793,219 and 2,793,220.

We have now discovered that unsaturated dicarboxylic acids having 16, 17, 18, 20, or 22 carbon atoms, will also dimerize under the influence of clay catalysts to yield novel tetracarboxylic acids of 32, 34, 36, 40, or 44 carbon atoms having unique and useful properties. This is unexpected in view of the fact that a commercial unsaturated dicarboxylic acid of 21 carbon atoms will not dimerize under the same conditions.

SUMMARY OF THE INVENTION

The invention comprises the dimers of unsaturated dicarboxylic acids selected from those having 16, 17, 18, 20 and 22 carbon atoms, inclusive. The invention also comprises the method of preparing the dimers of the invention.

The dimer acids of the invention are useful as corrosion inhibitors, epoxy resin curing agents, synthetic polymeric resin plasticizers and lubricants.

DETAILED DESCRIPTION OF THE PREFERRED EMBODIMENTS OF THE INVENTION

The method of the invention may be employed advantageously to dimerize unsaturated dicarboxylic acids of the described carbon atom content, including mixtures of monounsaturated and polyunsaturated dicarboxylic acids. Exemplary of the unsaturated dicarboxylic acids are:

hexadec-8-enedioic acid;
eicose-8,12-dienedioic acid;
7-vinyl-tetradecanedioic acid;
8-vinyl-octadec-10-enedioic acid;
8,13-dimethyleicose-8,12-dienedioic acid; and
octadec-9-enedioic acid.

The dimerization is carried out by heating the dicarboxylic acids in the presence of a catalytic proportion of a clay catalyst.

The unactivated clay catalysts employed in the process of the invention are well known and commercially available. Representative of such clays are hectorite, montmorillonite, attapulgite, sepiolite, bentonite, per se or in combination with montmorillonite. The clays are employed in catalytic proportions, generally within the range of from 1 to 10 percent by weight of dicarboxylic acid.

Advantageously employed in the method of the invention is a modifying proportion of a catalyst modifier, i.e., alkaline earth or alkali metal salt. Particularly advantageously, use of a lithium salt modifier effects the selectivity of dimer product in the reaction and also improves (reduces) coloration of the product dimer acids.

The proportion of alkali metal salt employed is generally within the range of from 0.5 to 6 milliequivalent (meq) per gram of clay catalyst employed.

Referring now to the accompanying drawing, a representative process of the invention will be described.

As shown in the drawing, a suitable reactor vessel 1 is charged with dicarboxylic acids containing 16, 17, 18, 20 or 22 carbon atoms, 1 to 10 percent by weight of an unactivated clay catalyst, and water (0.5-5 percent by weight of dicarboxylic acid). A modifying proportion of an alkali or alkaline earth metal salt may also be charged to vessel 1. The charge is heated to a temperature within the range of from 180° C. to 280° C. under autogenous pressures. The heating is continued until the dicarboxylic acid has polymerized. This usually requires a heating time within the range of about 2 to 5 hours; preferred conditions being about 4 hours at circa 245° C. The reaction mixture is cooled to about 100° C. and about 1 weight percent of phosphoric acid is added. The mixture is stirred for 1 hour then the contents of the reactor vessel 1 are discharged through a conduit line 2 into filter 3, through a conduit line 4 into a wiped film still 5 from which the residual unpolymerized acids are distilled through line 6 and are cooled and condensed into a receiver 7. A mixture of product dimeric acids is withdrawn through conduit line 8 into a receiving tank 9.

Distillation temperatures of 200°-300° C., at pressures of about 0.05-50 millimeters of mercury, are preferably maintained, but are not especially critical.

The following examples describe the manner and process of making and using the invention and set forth the best mode contemplated by the inventor of carrying out the invention, but are not to be construed as limiting. Example 4 is not an example of the present invention but is included to illustrate the inability of a $C_{21}$-diacid to dimerize.

EXAMPLE 1

A charge of 150 gms of ULB-20* (OKAMURA OIL MILL Ltd.) was heated in an autoclave with 8 weight percent montmorillonite clay and 14 weight percent water at 260° C. for 3 hours. The crude product was treated with phosphoric acid and filtered. Monomer was then distilled in a Smith wiped-film molecular still at 270° C. and 0.5 mm Hg. Yields and product characterization are given in the Table.

*ULB-20 is a mixture of dicarboxylic acids having the following composition:

| DIACID | % BY WEIGHT |
|---|---|
| $HOOC-(CH_2)_6-CH=CH-(CH_2)_6-COOH$ | 4-9% |
| $HOOC-(CH_2)_6-CH=CH-(CH_2)_2-CH=CH-(CH_2)_6-COOH$ | 35-52% |

-continued

| DIACID | % BY WEIGHT |
|---|---|
| HOOC—(CH$_2$)$_5$—CH—(CH$_2$)$_6$—COOH<br>　　　　　　　\|<br>　　　　　　CH=CH$_2$ | 2–4% |
| HOOC—(CH$_2$)$_6$—CH—CH$_2$—CH=CH—(CH$_2$)$_6$—COOH<br>　　　　　　　\|<br>　　　　　　CH=CH$_2$ | 30–40% |

EXAMPLE 2

A charge of 150 gms of ULB-20 was heated in an autoclave with 4 weight percent montmorillonite clay, 5 weight percent water, and a small amount of Li$_2$CO$_3$ (to modify the clay) at 245° C. for 4 hours. The crude product was treated with phosphoric acid then filtered and split in a Smith wiped-film molecular still at 255° C. and 0.7 mm Hg. An aliquot of the split product was analyzed by high pressure liquid chromatography on a Spherogel column and the acid number (ASTM D1980) and Cannon-Fenske viscosity of the dimer product (ASTM D446-74) were measured The results are given in the Table below.

EXAMPLE 3

The procedure of Example 2, supra., was repeated except that the ULB-20 as used therein was replaced with an equal proportion of IPU-22** (OKAMURA OIL MILL, Ltd., supra). The analytical results are set forth in the Table, below.

**IPU-22 is a mixture of dicarboxylic acids, the main component being a diacid of the formula:

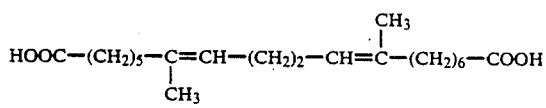

TABLE
Dimerization of Unsaturated Diacids
Product Yields and Properties

|  | Example 1 | Example 2 | Example 3 |
|---|---|---|---|
| % Dimer Split | 60.5 | 68.0 | 55.7 |
| % Monomer | 19 | 20 | 46 |
| Acid Number | 287 | 309 | 284 |
| Viscosity, cps @ 25° C. | 180,000+ | 180,000+ | 180,000+ |
| Viscosity, cps @ 100° C. | 1100 | 550 | 320 |

EXAMPLE 4

The procedure of Example 2 was repeated except that the ULB-20* as used therein was replaced with 200g of C$_{21}$ diacid*** (Westvaco 1550). Analysis of the product by high pressure liquid chromatography on a Spherogel column showed the product to be identical tot he starting material, indicating that dimerization did not occur.

***C$_{21}$ diacid contains a mixture of the following isomers:

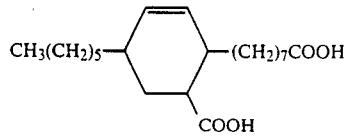

6-carboxy-4-hexyl-2-cyclohexene-1-octanoic acid

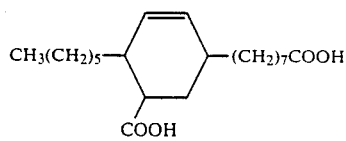

5-carboxy-4-hexyl-2-cyclohexene-1-octanoic acid

What is claimed is:

1. Dimers of dimerizable unsaturated dicarboxylic acids selected from those having 16, 17, 18, 20, and 22 carbon atoms.

2. Dimers of claim 1 wherein the acid selected is one containing 20 carbon atoms.

3. Dimers of claim 1 wherein the acid is selected from the group consisting of eicose-8,12-dienedioic acid or 8-vinyl-octadec-10-enedioic acid.

4. Dimers of claim 1 wherein the acid is 8,13-dimethyleicose-8,12-dienedioic acid.

5. Dimers of claim 1 wherein the acid is selected from the group consisting of hexadec-8-enedioic acid or 7-vinyl-tetradecanedioic acid.

6. Dimers of claim 1 wherein the acid is octadec-9-enedioic acid.

7. A method of preparing tetracarboxylic acids having 32, 34, 36, 40 or 44 carbon atom, which comprises;
providing a dimerizable, unsaturated aliphatic dicarboxylic acid selected from the group consisting of those containing 16, 17, 18, 20 and 22 carbon atoms; and
heating the selected acid in the presence of a catalytic proportion of an unactivated clay, from 0.5 to 6 milliequivalent per gram of clay catalyst of an alkali or alkaline earth metal salt, and 0.05 to 5 percent by weight of acid, of water.

8. The method of claim 7 wherein the unactivated clay is montmorillonite.

9. The method of claim 7 wherein the modifying salt is lithium carbonate.

10. The method of claim 7 wherein the modifying salt is lithium hydroxide.

11. The method of claim 7 wherein the heating is to a temperature of 235–265° C.

12. The method of claim 7 wherein the heating is under a pressure of 80–150 psig.

* * * * *